(12) United States Patent
Kang et al.

(10) Patent No.: US 11,247,958 B2
(45) Date of Patent: Feb. 15, 2022

(54) METHOD AND APPARATUS FOR DECOMPOSING PHENOLIC BY-PRODUCT

(71) Applicant: LG CHEM, LTD., Seoul (KR)

(72) Inventors: Min Suk Kang, Daejeon (KR); Sang Beom Lee, Daejeon (KR); Joon Ho Shin, Daejeon (KR)

(73) Assignee: LG Chem, Ltd., Seoul (KR)

( * ) Notice: Subject to any disclaimer, the term of this patent is extended or adjusted under 35 U.S.C. 154(b) by 12 days.

(21) Appl. No.: 16/975,331

(22) PCT Filed: Oct. 15, 2019

(86) PCT No.: PCT/KR2019/013517
§ 371 (c)(1),
(2) Date: Aug. 24, 2020

(87) PCT Pub. No.: WO2020/130314
PCT Pub. Date: Jun. 25, 2020

(65) Prior Publication Data
US 2020/0407300 A1 Dec. 31, 2020

(30) Foreign Application Priority Data

Dec. 20, 2018 (KR) .......................... 10-2018-0166578

(51) Int. Cl.
| | |
|---|---|
| *C07C 37/74* | (2006.01) |
| *B01D 3/00* | (2006.01) |
| *B01D 3/14* | (2006.01) |
| *B01D 3/32* | (2006.01) |
| *B01D 3/42* | (2006.01) |
| *C07C 39/16* | (2006.01) |

(52) U.S. Cl.
CPC .............. *C07C 37/74* (2013.01); *B01D 3/009* (2013.01); *B01D 3/146* (2013.01); *B01D 3/32* (2013.01); *B01D 3/4266* (2013.01); *C07C 39/16* (2013.01)

(58) Field of Classification Search
CPC ................................ C07C 37/74; B01D 3/146
See application file for complete search history.

(56) References Cited

U.S. PATENT DOCUMENTS

| | | | |
|---|---|---|---|
| 3,850,996 A | 11/1974 | Nixon | |
| 4,158,611 A | 6/1979 | Cooke | |
| 4,246,203 A | 1/1981 | Wirth | |
| 5,240,568 A | 8/1993 | Chan et al. | |
| 5,457,244 A * | 10/1995 | Dyckman | C07C 37/86 568/754 |
| 5,785,823 A | 7/1998 | Meurer et al. | |
| 5,795,823 A | 8/1998 | Avanzino et al. | |
| 8,044,248 B2 * | 10/2011 | Palmer | C07C 37/20 568/728 |

FOREIGN PATENT DOCUMENTS

| | | |
|---|---|---|
| EP | 0168358 A1 | 1/1986 |
| EP | 3680226 A1 | 7/2020 |
| JP | S52-35656 B1 | 9/1977 |
| JP | S60-123434 A | 7/1985 |
| KR | 10-0161038 B1 | 1/1999 |
| KR | 10-0262026 B1 | 7/2000 |
| KR | 10-2003-0060979 A | 7/2003 |
| KR | 10-0665764 B1 | 1/2007 |
| KR | 10-2010-0132963 A | 12/2010 |
| KR | 10-2014-0127611 A | 11/2014 |
| KR | 10-2015-0073972 A | 7/2015 |
| WO | 2017-111357 A1 | 6/2017 |

* cited by examiner

*Primary Examiner* — Sikarl A Witherspoon
(74) *Attorney, Agent, or Firm* — Dentons US LLP

(57) ABSTRACT

The present disclosure relates to a method and an apparatus for decomposing a phenolic by-product generated in a bisphenol A preparation process, the method including: a step (S10) of feeding the phenolic by-product to a multistage reactive distillation column; a step (S20) of separating the phenolic by-product into an upper discharge stream containing an active component, a side discharge stream containing acetophenone, and a bottom discharge stream containing tar by the multistage reactive distillation column; and a step (S30) of mixing the side discharge stream discharged from the multistage reactive distillation column and the bottom discharge stream discharged from the multistage reactive distillation column to form a mixed discharge stream.

13 Claims, 5 Drawing Sheets

METHOD AND APPARATUS FOR DECOMPOSING PHENOLIC BY-PRODUCT

CROSS-REFERENCE TO RELATED APPLICATIONS

This application is a National Phase entry pursuant to U.S.C. § 371 of International Application No. PCT/KR2019/013517 filed on Oct. 15, 2019, and claims the benefit of and priority to Korean Patent Application No. 10-2018-0166578, filed on Dec. 20, 2018, all of which are hereby incorporated by reference in their entirety for all purposes as if fully set forth herein.

TECHNICAL FIELD

The present invention relates to a method and an apparatus for decomposing a phenolic by-product generated in a bisphenol A preparation process.

BACKGROUND ART

Bisphenol A is prepared by performing a condensation reaction of phenol and acetone in the presence of an acid catalyst and then a separation and purification process. A phenolic by-product is generated in such a bisphenol A preparation process, and the phenolic by-product contains an active component such as phenol, cumene, or alpha-methylstyrene, thus a phenolic by-product decomposition process for recovering the active component has been performed. The decomposition process is performed using a decomposition apparatus in which a reactor and a distillation tower are separated from each other, or a reactor and a distillation tower are integrated with each other. This will be described with reference to the drawing as follows.

FIG. 3 illustrates a decomposition process performed by a decomposition apparatus in which a reactor 100 and a distillation tower 200 are separated, a by-product added to the reactor 100 is thermally cracked, tar contained in the by-product is discharged through a bottom portion of the reactor 100, and residual components are discharged through an upper portion of the reactor 100 and added to the distillation tower 200. Next, a reduced-pressure distillation is performed in the distillation tower 200, acetophenone and residual by-products are discharged through a bottom portion of the distillation tower 200, and an active component and a light component are discharged through an upper portion of the distillation tower 200, such that the active component is recovered. Such a decomposition process may increase a recovery rate of the active component, but has problems in that an installation space for equipment is required and a consumption rate of thermal energy is high due to a decomposition process and a reduced-pressure distillation process that are separately performed.

Unlike the decomposition process illustrated in FIG. 3, FIG. 4 illustrates a decomposition process performed by a decomposition apparatus including a reactor 300 in which a distillation tower is integrated, a by-product added to the reactor 300 is subjected to thermal cracking and pressure distillation, tar, acetophenone, and residual by-products contained in the by-product are discharged through a bottom portion of the reactor 300, and an active component and a light component are discharged through an upper portion of the reactor 300, such that the active component is recovered. Such a decomposition process may reduce an installation space for equipment and may reduce a consumption rate of thermal energy, but has problems in that a polymerization phenomenon (for example, dimerization reaction or polymerization reaction of alpha-methylstyrene) of the active component in the pressure distillation process occurs, and thus a recovery rate of the active component is reduced.

Accordingly, a decomposition process and a decomposition apparatus that are capable of efficiently recovering an active component from a phenolic by-product generated in a bisphenol A preparation process have been required.

DISCLOSURE

Technical Problem

In order to solve the problems mentioned in the background art, an object of the present invention is to provide a method and an apparatus for decomposing a phenolic by-product that are capable of reducing a consumption rate of thermal energy in a decomposition process and increasing a recovery rate of an active component by improving the decomposition process of the phenolic by-product generated in a bisphenol A preparation process.

Technical Solution

In one general aspect, there is provided a method for decomposing a phenolic by-product generated in a bisphenol A preparation process, the method including: a step (S10) of feeding the phenolic by-product to a multistage reactive distillation column; a step (S20) of separating the phenolic by-product into an upper discharge stream containing an active component, a side discharge stream containing acetophenone, and a bottom discharge stream containing tar by the multistage reactive distillation column; and a step (S30) of mixing the side discharge stream discharged from the multistage reactive distillation column and the bottom discharge stream discharged from the multistage reactive distillation column to form a mixed discharge stream.

In another aspect, there is provided an apparatus for decomposing a phenolic by-product generated in a bisphenol A preparation process, the apparatus including: a multistage reactive distillation column separating the phenolic by-product into an upper discharge stream containing an active component, a side discharge stream containing acetophenone, and a bottom discharge stream containing tar; and a moving line system including a side discharge stream moving line through which the side discharge stream is discharged and moved, and a bottom discharge stream moving line through which the bottom discharge stream is discharged and moved, wherein the side discharge stream moving line and the bottom discharge stream moving line are connected to each other so that the side discharge stream and the bottom discharge stream are joined with each other to form a mixed discharge stream.

Advantageous Effects

According to the present invention, an operation of the multistage reactive distillation column is performed within a range of a normal pressure, such that a polymerization phenomenon of an active component may be prevented, thereby increasing a recovery rate of the active component.

In addition, according to the present invention, a viscosity of a bottom discharge stream is reduced by mixing a side discharge stream with the bottom discharge stream containing tar and having a high viscosity, such that movability and storability of tar contained in the bottom discharge stream may be increased.

In addition, according to the present invention, a heat exchange between a mixed discharge stream and the phenolic by-product is performed, the mixed discharge stream obtained by mixing the side discharge stream and the bottom discharge stream, such that a consumption rate of thermal energy in the phenolic by-product decomposition process may be reduced.

BEST MODE

The terms and words used in the description and claims of the present invention are not to be construed as general or dictionary meanings but are to be construed as meanings and concepts meeting the technical ideas of the present invention based on a principle that the inventors can appropriately define the concepts of terms in order to describe their own inventions in the best mode.

In the present invention, the term "stream" may mean a flow of a fluid in a process and may also mean a fluid itself flowing through a moving line (pipe). In addition, the fluid may be construed as a gas, liquid, or fluid state in a process of moving the respective apparatuses.

In the present specification, the term "upper portion" may mean an upper part of two regions obtained by vertically dividing each apparatus in a length direction or a height direction, and the term "bottom portion" may mean a lower part of two regions obtained by vertically dividing each apparatus in a length direction or a height direction. In addition, the term "side" may mean a side surface that exists along a length direction of each apparatus (specifically, a left side or a right side along the length direction).

In the present specification, the term "moving line" may mean a structure including a pipe connecting the respective apparatuses to each other or a transfer line, and the term "moving line" may have actually the same meaning as the pipe.

Hereinafter, the present invention will be described in detail.

The present invention relates to a method for decomposing a phenolic by-product generated in a bisphenol A preparation process, and the decomposition method including: a step (S10) of feeding the phenolic by-product to a multistage reactive distillation column; a step (S20) of separating the phenolic by-product into an upper discharge stream containing an active component, a side discharge stream containing acetophenone, and a bottom discharge stream containing tar by the multistage reactive distillation column; and a step (S30) of mixing the side discharge stream discharged from the multistage reactive distillation column and the bottom discharge stream discharged from the multistage reactive distillation column to form a mixed discharge stream. The method for decomposing a phenolic by-product of the present invention will be described in detail with reference to the drawings.

Figure 1:
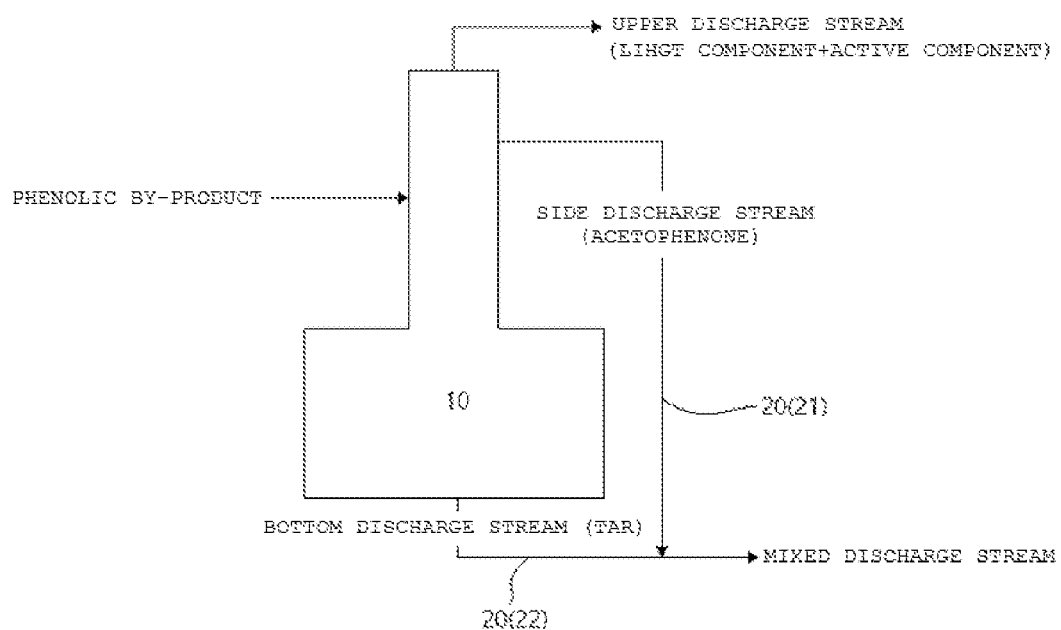
FIG. 1 is a reference view for describing a method and an apparatus for decomposing a phenolic by-product according to an exemplary embodiment of the present invention.

Referring to FIG. 1, according to an exemplary embodiment of the present invention, the step (S10) includes a process of feeding a phenolic by-product to a multistage reactive distillation column 10. The phenolic by-product is generated in the bisphenol A preparation process, and may contain one or more selected from the group consisting of phenol, alpha-methylstyrene, cumene, acetophenone, cumylphenol, dimers of alpha-methylstyrene, bisphenol A (BPA) and residual by-products.

According to an exemplary embodiment of the present invention, the step (S20) includes a process of separating (decomposing) the phenolic by-product by thermal cracking. That is, the phenolic by-product is separated into the upper discharge stream containing an active component, the side discharge stream containing acetophenone, and the bottom discharge stream containing tar by thermal cracking the phenolic by-product added to the multistage reactive distillation column 10.

According to an exemplary embodiment of the present invention, in order to perform thermal cracking on the phenolic by-product, an operation of the multistage reactive distillation column 10 may be performed at 0.1 bar (10 kPa) to 3.0 bar (300 kPa), 0.1 bar (10 kPa) to 2.0 bar (200 kPa), or 0.1 bar (10 kPa) to 1.0 bar (100 kPa). In a case where the operation of the multistage reactive distillation column 10 is performed within the pressure range, a polymerization phenomenon (for example, dimerization or polymerization of alpha-methylstyrene) of the active component in the multistage reactive distillation column 10 is minimized, such that a yield of the active component may be increased. In addition, since the side discharge stream containing acetophenone may be separated from the phenolic by-product without thermal cracking under a pressure condition, a consumption rate of thermal energy consumed during thermal cracking may be reduced.

In the case where the operation of the multistage reactive distillation column 10 is performed within the above pressure range, an operation of the multistage reactive distillation column 10 during thermal cracking may be performed at 260° C. to 370° C., 290° C. to 370° C., or 300° C. to 350° C. In a case where the thermal cracking is performed in the above temperature range, a yield of the active component may be increased, acetophenone contained in the phenolic by-product may be smoothly discharged through the side discharge stream. That is, a purity and a yield of the active component may be increased by minimizing a content of acetophenone that acts as an impurity in the upper discharge stream.

According to an exemplary embodiment of the present invention, the upper discharge stream separated by thermal cracking of the phenolic by-product is discharged through an upper portion of the multistage reactive distillation column 10, and the upper discharge stream contains an active component. The upper discharge stream may contain an active component together with a light component. Accordingly, the upper discharge stream may be subjected to a purification process for recovering the active component. The active component may be one or more selected from the group consisting of phenol, alpha-methylstyrene, and cumene. The respective components of such an active component may be obtained as a product as it is or may be reused in the bisphenol A preparation process. In addition, the light component is generated in the thermal cracking process, and may be toluene, styrene, or the like having a boiling point lower than that of the active component.

The active component is discharged through the upper portion (specifically, top) of the multistage reactive distillation column 10 together with the light component, which may increase a recovery rate of the active component from the phenolic by-product. That is, in a case where the active component is discharged through the upper portion of the multistage reactive distillation column 10 separately from the light component (for example, in a case where the light component is discharged through the upper portion of the multistage reactive distillation column 10, and the active component is discharged through a side of the multistage reactive distillation column 10), a part of the active component is discharged through the upper portion of the multistage reactive distillation column 10 while being contained in the light component discharged through the upper portion of the multistage reactive distillation column 10, which causes a reduction of a recovery rate of the active component. However, in the present invention, the active component and the light component are discharged together through the upper portion of the multistage reactive distillation column 10, such that a loss of the active component is minimized and a recovery rate of the active component may thus be increased.

Such an upper discharge stream may be additionally subjected to a purification process of separating the active component and the light component, if necessary.

According to an exemplary embodiment of the present invention, the side discharge stream separated by thermal cracking of the phenolic by-product is discharged through the side of the multistage reactive distillation column 10, and the side discharge stream contains acetophenone. Since the acetophenone acts as an impurity that is not required as an active component, the acetophenone contained in the phenolic by-product is mostly contained in the side discharge stream and is discharged through the side of the multistage reactive distillation column 10. Specifically, a content of acetophenone derived from the phenolic by-product contained in the side discharge stream may be 99 wt % or more, 99.5 wt % or more, or 99.6 wt % to 100 wt %. For example, the content of acetophenone contained in the side discharge stream is 99 wt % or more based on 100 wt % of acetophenone contained in the phenolic by-product. In a case where the content of acetophenone contained in the side discharge stream is within the above range, a content of acetophenone in the active component is minimized, such that a yield of the active component may be increased. In addition, in the case where the content of the acetophenone contained in the side discharge stream is within the above range, it is possible to contribute to the reduction of a viscosity of the bottom discharge stream, which will be described below.

In addition, the side discharge stream may contain isopropylphenol and other by-products generated in the thermal cracking process in addition to acetophenone derived from the phenolic by-product. For example, the side discharge stream may contain 40 wt % to 50 wt % of acetophenone, 20 wt % to 30 wt % of isopropylphenol, and 25 wt % to 35 wt % of other by-products, based on 100 wt % of the side discharge stream.

According to an exemplary embodiment of the present invention, the side discharge stream may be discharged through a side outlet provided at a stage within the top 50% to 90%, 50% to 85%, or 50% to 80% of a total number of stages of the multistage reactive distillation column 10. For example, in a case where the total number of stages of the multistage reactive distillation column 10 is 100, the side outlet is positioned at a stage corresponding to $50^{th}$ to $90^{th}$ from the top. Specifically, in a case where the total number of stages of the multistage reactive distillation column 10 is 30, the side outlet may be positioned at the $15^{th}$ stage. The side discharge stream is discharged through the side outlet provided at a stage within the above range, such that acetophenone is efficiently separated, thereby increasing a recovery rate and purity of the active component.

According to an exemplary embodiment of the present invention, the bottom discharge stream separated by thermal cracking of the phenolic by-product is discharged through the bottom portion of the multistage reactive distillation column 10, and the bottom discharge stream contains tar. The tar is a black or brown viscous oil phase substance, and may be recovered later to be used as fuel and the like.

According to an exemplary embodiment of the present invention, the step (S30) includes a process of mixing the side discharge stream discharged from the multistage reactive distillation column 10 and the bottom discharge stream discharged from the multistage reactive distillation column 10 to form a mixed discharge stream.

A viscosity of the mixed discharge stream is reduced than that of the bottom discharge stream by the step (S30), which may increase movability and storability of tar having a high viscosity. That is, tar having a high viscosity is not easily transferred and stored at room temperature, but in the present invention, since the viscosity of the bottom discharge stream is reduced by mixing the side discharge stream with the bottom discharge stream, movability and storability of tar contained in the bottom discharge stream may be increased.

Figure 2:
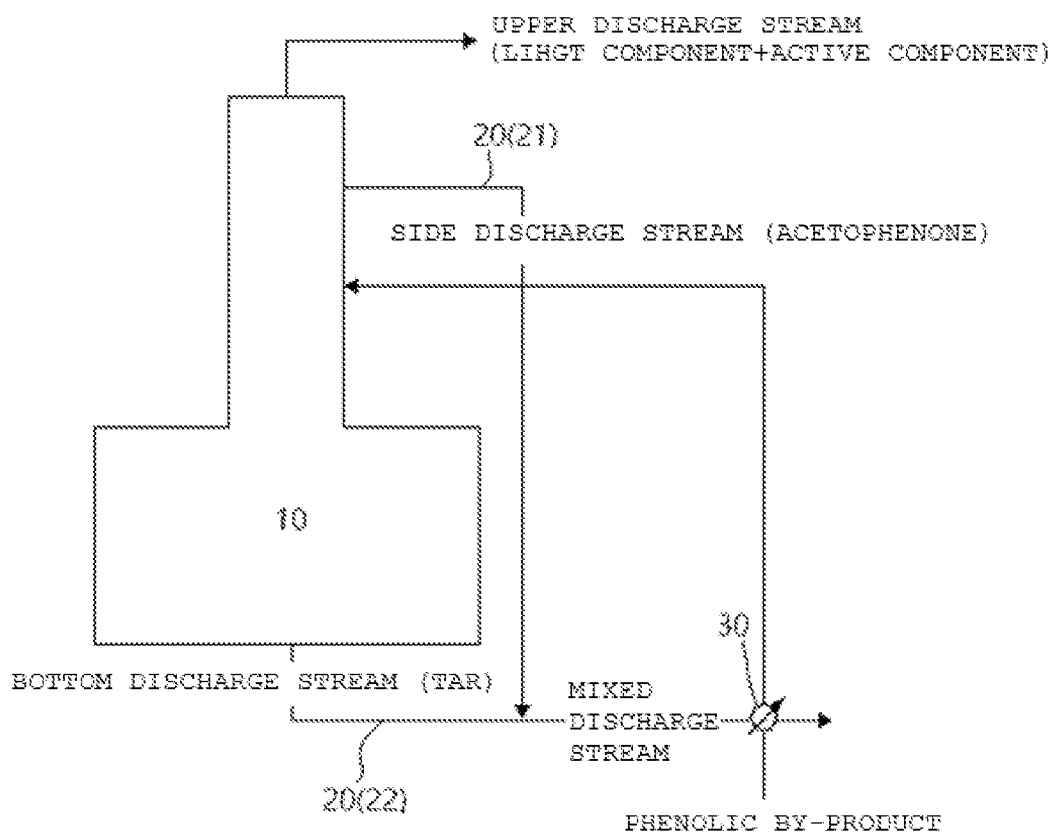
FIG. 2 is a reference view for describing a method and an apparatus for decomposing a phenolic by-product according to another exemplary embodiment of the present invention.

According to an exemplary embodiment of the present invention, a heat exchange between the phenolic by-product and the mixed discharge stream may be performed (see FIG. 2). That is, the phenolic by-product may be fed to the multistage reactive distillation column 10 after being subjected to the heat exchange with the mixed discharge stream by a heat exchanger 30. The phenolic by-product is added to the multistage reactive distillation column 10 through the heat exchange while being in a high temperature state, such that energy consumed to operate a heater of the multistage reactive distillation column 10 is reduced, whereby a consumption rate of thermal energy consumed during thermal cracking of the phenolic by-product may be reduced.

Meanwhile, the present invention relates to an apparatus for decomposing a phenolic by-product generated in a bisphenol A preparation process, and the decomposition apparatus includes a multistage reactive distillation column 10 and a moving line system 20.

According to an exemplary embodiment of the present invention, the multistage reactive distillation column 10 separates the phenolic by-product into an upper discharge stream containing an active component, a side discharge stream containing acetophenone, and a bottom discharge stream containing tar. As such a multistage reactive distillation column 10, an apparatus in which a reactor and a multistage distillation tower are integrated may be used.

Here, according to an exemplary embodiment of the present invention, a side outlet through which the side discharge stream is discharged may be provided at a stage within the top 50% to 90%, 50% to 85%, or 50% to 80% of a total number of stages of the multistage reactive distillation column 10. For example, in a case where the total number of stages of the multistage reactive distillation column 10 is 100, the side outlet is positioned at a stage corresponding to $50^{th}$ to $90^{th}$ from the top. The side outlet is provided at a stage within the above range, such that acetophenone is efficiently separated, thereby increasing a recovery rate and purity of the active component.

In addition, according to an exemplary embodiment of the present invention, an upper outlet through which the upper discharge stream is discharged may be provided at an upper portion of the multistage reactive distillation column 10. The upper outlet is provided at the upper portion of the multistage reactive distillation column 10, such that a recovery rate of the active component contained in the upper discharge stream may be increased.

According to an exemplary embodiment of the present invention, the moving line system 20 includes a moving pipe or a moving line that connects the respective apparatuses so that the respective streams are moved to the respective apparatuses. In particular, the moving line system includes a side discharge stream moving line 21 through which the side discharge stream is discharged and moved and a bottom discharge stream moving line 22 through which the bottom discharge stream is discharged and moved. Here, the side discharge stream moving line 21 and the bottom discharge stream moving line 22 are connected to each other so that the side discharge stream and the bottom discharge stream are joined with each other.

The side discharge stream and the bottom discharge stream are joined with each other by the connection of the side discharge stream moving line 21 and the bottom discharge stream moving line 22. In this case, the side discharge stream and the bottom discharge stream are mixed with each other by the joining, such that a mixed discharge stream may be formed, or the side discharge stream and the bottom discharge stream converge at a separate mixing apparatus (for example, drum) and are mixed with each other by the joining, such that a mixed discharge stream may be formed.

Meanwhile, according to an exemplary embodiment of the present invention, the apparatus for decomposing a phenolic by-product may further include a heat exchanger 30 performing a heat exchange between the phenolic by-product and the mixed discharge stream. As the heat exchanger 30, a shell-tube type heat exchanger, a spiral type heat exchange, or a plate type heat exchanger may be used.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

Example 1

Decomposition of a phenolic by-product was performed by using a decomposition apparatus and a decomposition process flowchart illustrated in FIG. 1. Specifically, the phenolic by-product having compositions of Table 1 was fed to an inlet provided at a side of a multistage reactive distillation column 10 having 30 stages in total and thermal cracking (thermal cracking temperature: 330° C., thermal cracking pressure: normal pressure) of the phenolic by-product (flow rate: 1000 kg/hr) was performed.

Through the thermal cracking, the phenolic by-product was separated into an upper discharge stream containing an active component, a side discharge stream containing acetophenone, and a bottom discharge stream containing tar, and then a process of discharging the respective streams from the multistage reactive distillation column 10 was continuously performed. Through the thermal cracking, about 99 wt % of acetophenone contained in the phenolic by-product was separated through the side discharge stream, and tar corresponding to about 30 wt % of the feed weight was discharged through the bottom discharge stream.

Meanwhile, the side discharge stream was discharged and moved through a side outlet provided at a position corresponding to the $15^{th}$ stage of the multistage reactive distillation column, and a side discharge stream moving line 21, and was joined and mixed with the bottom discharge stream to form a mixed discharge stream. In addition, the upper discharge stream was discharged through an upper outlet provided at an upper portion of the multistage reactive distillation column 10.

Example 2

Decomposition of a phenolic by-product was performed by using a decomposition apparatus and a decomposition process flowchart illustrated in FIG. 2. Specifically, the phenolic by-product having compositions of Table 1 was fed to an inlet provided at a side of a multistage reactive distillation column 10 having 30 stages in total and thermal cracking (thermal cracking temperature: 330° C., thermal cracking pressure: normal pressure) of the phenolic by-product (flow rate: 1000 kg/hr) was performed.

Through the thermal cracking, the phenolic by-product was separated into an upper discharge stream containing an active component, a side discharge stream containing acetophenone, and a bottom discharge stream containing tar, and then a process of discharging the respective streams from the multistage reactive distillation column 10 was continuously performed. Through the thermal cracking, about 99 wt % of acetophenone contained in the phenolic by-product was separated through the side discharge stream, and tar corresponding to about 30 wt % of the feed weight was discharged through the bottom discharge stream.

Meanwhile, the side discharge stream was discharged and moved through a side outlet provided at a position corresponding to the $15^{th}$ stage of the multistage reactive distillation column, and a side discharge stream moving line 21, and was joined and mixed with the bottom discharge stream to form a mixed discharge stream. The formed mixed discharge stream was subjected to a heat exchange with the phenolic by-product, and the heat exchanged phenolic by-product was fed to the multistage reactive distillation column 10 through the inlet provided at the side of the multistage reactive distillation column 10. In addition, the upper discharge stream was discharged through an upper outlet provided at an upper portion of the multistage reactive distillation column 10.

Comparative Example 1

Figure 3:
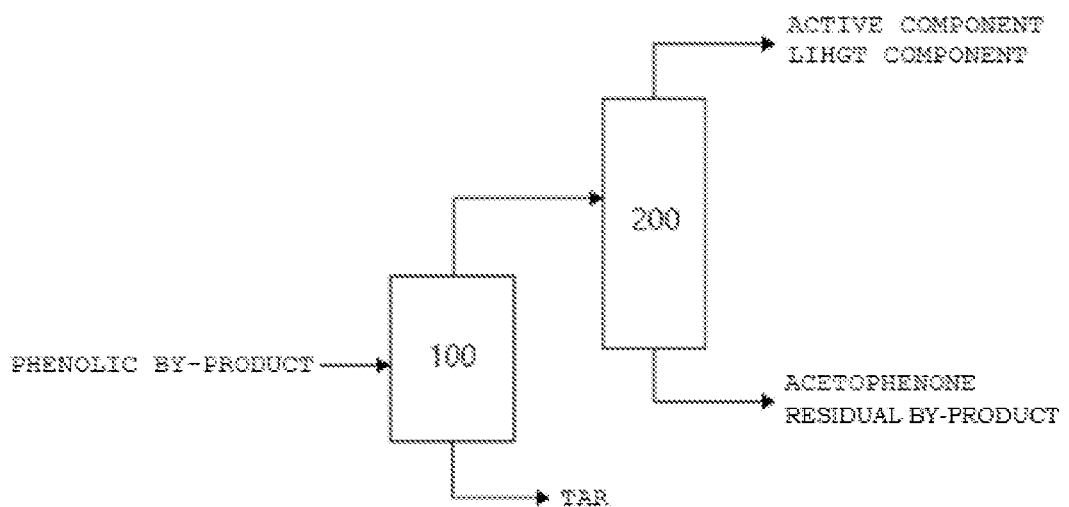
FIG. 3 is a reference view for describing a method and an apparatus for decomposing a phenolic by-product according to Comparative Example 1 of the present invention.

Decomposition of a phenolic by-product was performed by using a decomposition apparatus and a decomposition process flowchart illustrated in FIG. 3. Specifically, the phenolic by-product having compositions of Table 1 was fed to a reactor 100 and thermal cracking (thermal cracking temperature: 330° C., thermal cracking pressure: normal pressure) of the phenolic by-product (flow rate: 1000 kg/hr) was performed. Through the thermal cracking, a stream containing tar was discharged through a bottom portion of the reactor 100, and a stream containing an active component and acetophenone was discharged through an upper portion of the reactor 100. In this case, through the thermal cracking, about 99 wt % of acetophenone contained in the phenolic by-product was separated through the upper portion of the reactor 100, and tar corresponding to about 30 wt % of the feed weight was generated. Thereafter, the stream containing an active component and acetonephenone discharged through the upper portion of the reactor 100 was added to a distillation tower 200 and was subjected to a reduced-pressure distillation process. After being subjected to the reduced-pressure distillation process, the stream containing an active component was discharged through an upper portion of the distillation tower 200, and the stream containing acetophenone was discharged through a bottom portion of the distillation tower 200.

Comparative Example 2

Figure 4:
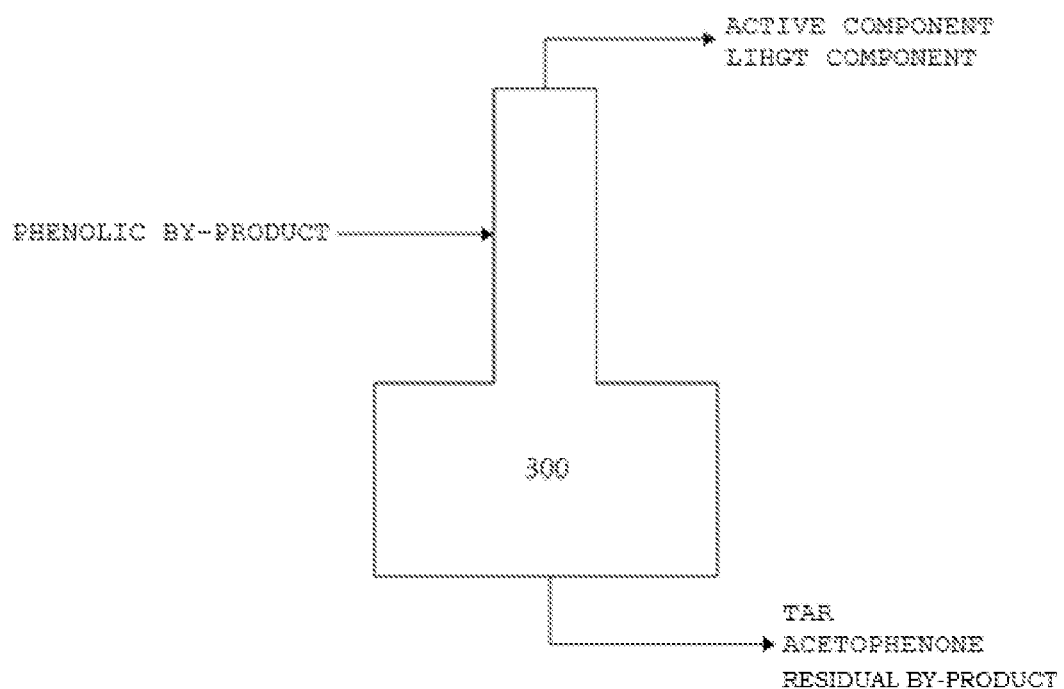
FIG. 4 is a reference view for describing a method and an apparatus for decomposing a phenolic by-product according to Comparative Example 2 of the present invention.

Decomposition of a phenolic by-product was performed by using a decomposition apparatus and a decomposition process flowchart illustrated in FIG. 4. Specifically, the phenolic by-product having compositions of Table 1 was fed to a multistage reactor 300 and thermal cracking (thermal cracking temperature: 330° C., thermal cracking pressure: pressurization) of the phenolic by-product (flow rate: 1000 kg/hr) was performed. Through the thermal cracking, a stream containing acetophenone and tar was discharged through a bottom portion of the reactor 300, and a stream containing an active component was discharged through an upper portion of the reactor 300. In this case, through the thermal cracking, about 99 wt % of acetophenone contained in the phenolic by-product was separated through the bottom portion of the reactor 300, and tar corresponding to about 30 wt % of the feed weight was generated.

Comparative Example 3

Figure 5:
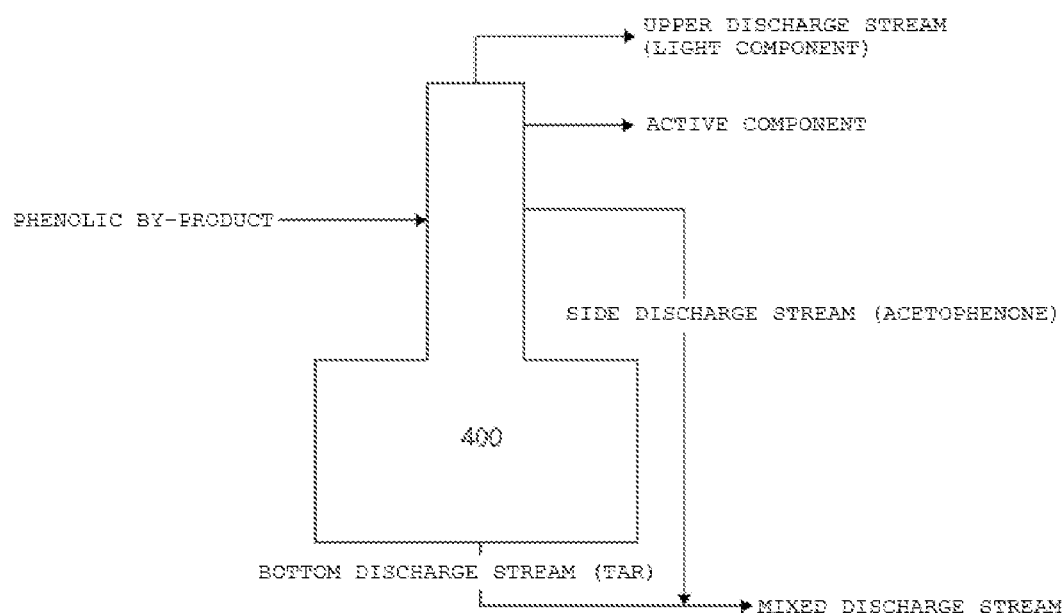
FIG. 5 is a reference view for describing a method and an apparatus for decomposing a phenolic by-product according to Comparative Example 3 of the present invention.

Decomposition of a phenolic by-product was performed by using a decomposition apparatus and a decomposition process flowchart illustrated in FIG. 5, and the decomposition of the phenolic by-product was performed with the same procedure as that of Example 1, except that an active component was separated through a side of a reactor 400 and a light component was separated through an upper portion of the reactor 400 (the active component and the light component were separately separated).

TABLE 1

| Composition of phenolic by-product (wt %) | |
| --- | --- |
| Phenol | 4.85 |
| Alpha-methylstyrene | 7.14 |
| Cumene | 0.00 |
| Acetophenone | 11.60 |
| Cumylphenol | 15.32 |
| Dimers of alpha-methylstyrene | 10.74 |
| Bisphenol A(BPA) | 11.56 |
| Others | 38.79 |
| Total | 100 |

Experimental Example

The compositions of the active composition and the thermal energy consumed in the thermal cracking process (consumed energy in the operation of the heater) that were obtained by Examples and Comparative Examples were confirmed, and the results are shown in Table 2.

TABLE 2

| Classification | | Example 1 | Example 2 | Comparative Example 1 | Comparative Example 2 | Comparative Example 3 |
| --- | --- | --- | --- | --- | --- | --- |
| Active component (%) | Phenol | 10.26 | 10.26 | 11.82 | 10.92 | 6.31 |
| | Alpha-methylstyrene | 20.95 | 20.95 | 18.76 | 4.54 | 16.97 |
| | Cumene | 3.16 | 3.16 | 3.05 | 3.97 | 1.65 |
| | Acetophenone | 0.04 | 0.04 | 0.04 | 0.04 | 0.04 |
| | Cumylphenol | 0.00 | 0.00 | 0.00 | 0.00 | 0.00 |
| | Dimers of alpha-methylstyrene | 0.00 | 0.00 | 0.00 | 0.00 | 0.00 |
| | Bisphenol A(BPA) | 0.00 | 0.00 | 0.00 | 0.00 | 0.00 |
| | Others | 1.95 | 1.95 | 1.96 | 1.94 | 0.03 |
| | Total | 36.36 | 36.36 | 35.63 | 21.40 | 25.00 |
| Consumed thermal energy (heat duty, Gcal/hr) | | 0.26 | 0.21 | 0.36 | 0.25 | 0.26 |
| Thermal cracking pressure (KG) | | 0 | 0 | 0 | 7 | 0 |

Referring to Table 2, it can be confirmed that in a case where the phenolic by-product was decomposed by the decomposition method according to the present invention, the recovery rate of the active component was high, and the thermal energy consumed in the decomposition process was low.

On the other hand, it can be confirmed that in the case of Comparative Example 1 in which the reactor and the distillation tower were separated, the thermal energy consumed in the decomposition process was very high. In addition, it may be expected that securement of an installation space and an increase in installation costs are required due to the separation of the reactor and the distillation tower.

In addition, it can be confirmed that in the case of Comparative Example 2 in which the thermal cracking was performed under a pressurization, from the fact that a ratio of alpha-methylstyrene was small, it could be seen that the active composition was polymerized, and thus the recovery rate of the active component was very low.

In addition, it can be confirmed that in the case of Comparative Example 3 in which only the active component was separated through the side of the multistage reactive distillation column, the recovery rate of the active component was reduced.

The invention claimed is:

1. A method for decomposing a phenolic by-product generated in a bisphenol A preparation process, the method comprising:
    a step of feeding the phenolic by-product to a multistage reactive distillation column;
    a step of separating the phenolic by-product into an upper discharge stream containing an active component, a side discharge stream containing acetophenone, and a bottom discharge stream containing tar by the multistage reactive distillation column; and
    a step of mixing the side discharge stream discharged from the multistage reactive distillation column and the bottom discharge stream discharged from the multistage reactive distillation column to form a mixed discharge stream.

2. The method of claim 1, wherein the phenolic by-product is subjected to a heat exchange with the mixed discharge stream by a heat exchanger and fed to the multistage reactive distillation column.

3. The method of claim 1, wherein the side discharge stream contains 99 wt % or more of acetophenone contained in the phenolic by-product.

4. The method of claim 1, wherein the side discharge stream is discharged through a side outlet provided at a stage within the top 50% to 90% of a total number of stages of the multistage reactive distillation column.

5. The method of claim 1, wherein a viscosity of the mixed discharge stream is lower than that of the bottom discharge stream.

6. The method of claim 1, wherein an operation pressure of the multistage reactive distillation column is 0.1 bar (10 kPa) to 3.0 bar (300 kPa).

7. An apparatus for decomposing a phenolic by-product generated in a bisphenol A preparation process, the apparatus comprising:
    a multistage reactive distillation column separating the phenolic by-product into an upper discharge stream containing an active component, a side discharge stream containing acetophenone, and a bottom discharge stream containing tar; and
    a moving line system including a side discharge stream moving line through which the side discharge stream is discharged and moved, and a bottom discharge stream moving line through which the bottom discharge stream is discharged and moved,
    wherein the side discharge stream moving line and the bottom discharge stream moving line are connected to each other so that the side discharge stream and the bottom discharge stream are joined with each other to form a mixed discharge stream.

8. The apparatus of claim 7, wherein a side outlet through which the side discharge stream is discharged is provided at a stage within the top 50% to 90% of a total number of stages of the multistage reactive distillation column.

9. The apparatus of claim 7, wherein an upper outlet through which the upper discharge stream is discharged is provided at an upper portion of the multistage reactive distillation column.

10. The apparatus of claim 7, further comprising a heat exchanger performing a heat exchange between the phenolic by-product and the mixed discharge stream.

11. The apparatus of claim 7, wherein an operation pressure of the multistage reactive distillation column is 0.1 bar (10 kPa) to 3.0 bar (300 kPa).

12. The method of claim 1, wherein the upper discharge stream comprises a light component.

13. The apparatus of claim 7, wherein the upper discharge stream comprises a light component.

* * * * *